(12) United States Patent
Legrand et al.

(10) Patent No.: US 9,182,329 B2
(45) Date of Patent: Nov. 10, 2015

(54) CELL FOR VERY HIGH PRESSURE ANALYSIS OF FLUID SAMPLES AND ASSOCIATED MEASURING METHOD

(71) Applicant: Vinci Technologies, Nanterre (FR)

(72) Inventors: Stephane Legrand, Paris (FR); Yannick Manissol, Dammartin sur Tigeaux (FR); Jeremy Delahais, Le Pont Marly (FR); Philippe Decrossas, Bois D'Arcy (FR)

(73) Assignee: Vinci Technologies, Nanterre (FR)

( * ) Notice: Subject to any disclaimer, the term of this patent is extended or adjusted under 35 U.S.C. 154(b) by 414 days.

(21) Appl. No.: 13/914,030

(22) Filed: Jun. 10, 2013

(65) Prior Publication Data
US 2013/0327131 A1    Dec. 12, 2013

(30) Foreign Application Priority Data
Jun. 12, 2012  (FR) ...................................... 12 55465

(51) Int. Cl.
  *G01N 1/00*     (2006.01)
  *G01N 1/44*     (2006.01)
  *G01N 33/28*    (2006.01)
  *G01N 21/03*    (2006.01)

(52) U.S. Cl.
  CPC .............. *G01N 1/44* (2013.01); *G01N 21/0317* (2013.01); *G01N 33/2823* (2013.01); *G01N 2201/08* (2013.01)

(58) Field of Classification Search
  CPC ......... G01N 1/10; G01N 1/28; G01N 1/2035; B01L 3/502715; B01L 2200/10
  USPC ................................................ 73/64.56, 863
  See application file for complete search history.

(56) References Cited

U.S. PATENT DOCUMENTS

| 6,827,842 B2 | 12/2004 | Beasley et al. |
| 2008/0016944 A1 | 1/2008 | Legrand |
| 2008/0252881 A1 | 10/2008 | Yakimoski et al. |

OTHER PUBLICATIONS

Castillo, Jimmy et al.: "Optical fiber extrinsic refractometer to measure RI of samples in a high pressure and temperature systems: Application to wax and asphaltene precipitation measurements", *Fuel*, 85 (2006), pp. 2220-2228.
Preliminary search report issued by French Patent Office for priority application FR 1255465 dated Jan. 8, 2013.

*Primary Examiner* — Hezron E Williams
*Assistant Examiner* — Rodney T Frank
(74) *Attorney, Agent, or Firm* — Frommer Lawrence & Haug LLP

(57) ABSTRACT

Disclosed is an analysis cell for the analysis, at very high pressure and high temperature, of fluid samples comprising a cylinder (1) in which an axially translatable piston is housed that defines, with the end walls of the cylinder, a closed compression chamber (10) in which the sample is confined, characterized in that the walls of said chamber (10) are provided with at least one bore (11) designed for sealably receiving an optical measuring element (2) movable inside said chamber between a retracted position retracted in the bore to allow the piston to pass, and a measuring position in which it protrudes in said chamber. The invention also relates to a method for detecting and/or measuring the quantity of solid matter using said cell.

14 Claims, 2 Drawing Sheets

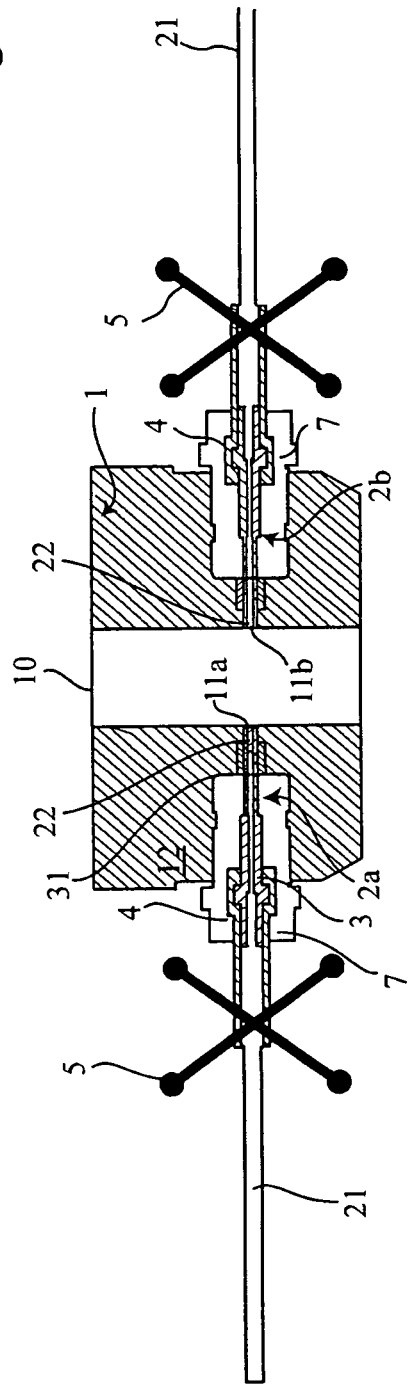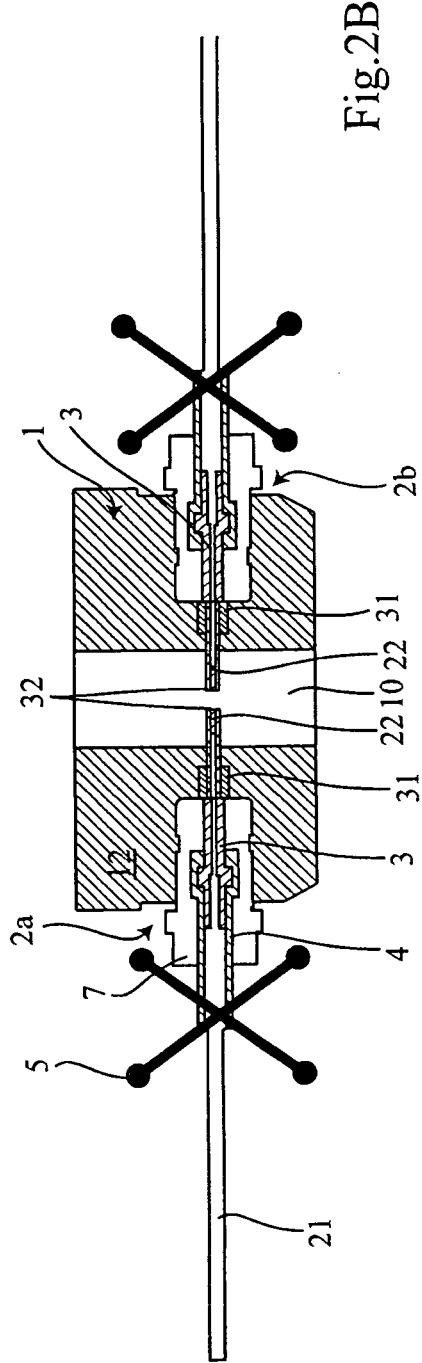

CELL FOR VERY HIGH PRESSURE ANALYSIS OF FLUID SAMPLES AND ASSOCIATED MEASURING METHOD

BACKGROUND

1. Field of the Invention

The present invention relates to an analysis cell for the analysis, at very high pressure and high temperature, of samples of fluids and a detection and measuring method using said cell to determine the conditions for the formation of solid particles and, if applicable, to measure the quantity of solid matter present in said samples.

2. Description of the Related Art

A high pressure and high temperature analysis cell is in particular applicable in the analysis of the thermodynamic and physicochemical properties of hydrocarbons.

These cells are used in the laboratory to perform tests and measurements making it possible to determine the composition of the crude oil taken from a prospecting site before the industrial and commercial exploitation thereof.

These measurements are more particularly intended to determine, precisely and sometimes directly on the site of the explored deposit, any presence of solid matter and the quantity thereof in the crude oil as well as the thermodynamic behavior of that matter during so-called "PVT" tests, i.e., pressure, volume and temperature.

The search for means for determining and predicting the thermodynamic conditions that may lead to the generation of solid particles in oil fluids during exploitation thereof has become very important in the field of oil exploration.

The formation of solid particles refers to the phenomena of asphaltene flocculation or precipitation, and the formation of paraffin (wax) or hydrate crystals.

In fact, at high pressure in the deposits, the asphaltenes are dissolved in the crude oil, which is therefore in a monophasic form.

However, during the extraction of the oil by drilling, the pressure decreases while rising toward the surface and the pressure/temperature pair assumes a first critical value called AOP (Asphaltene Onset Precipitation), which corresponds to the precipitation of asphaltenes. There is also a second critical value called WAT (Wax Appearance Temperature), at which wax crystals are likely to appear. For each sample, it is possible to predict the measurement of the bubble point, which corresponds, for a given temperature, to the state change pressure of the fluid (liquid-gas).

Thus, once equilibrium is broken, through temperature or pressure variations or through a simple change in the chemical composition, a solid phase forms that may cause plugging or accidental dirtying of the conduits for the drilling and/or pipelines, which is extremely detrimental to the exploitation of the well.

It is therefore necessary to provide, from samples taken from the bottom of the well (called "bottom hole samples"), the later behavior of its asphaltene/wax/hydrate components so as to prevent them from having a negative impact during all steps of the production, transport, and refining of hydrocarbons and so as to adapt the facilities and equipment dedicated thereto.

This need is further increased for so-called "new oils," which are primarily bituminous shales and deep oils extracted from "offshore" wells.

These heavy hydrocarbons and certain light oils are more problematic to exploit and transport, since the risk of the appearance of deposits of solid particles, during the rise in the wells and in the transport conduits due to significant pressure and temperature changes, is significantly greater than for traditional hydrocarbons.

The anticipation and/or neutralization of the risk of solid deposits is therefore a new challenge for the oil industry, which is seeking, for logistical and therefore economic reasons, guarantees with respect to the fluidity of the oil during all steps of the exploitation.

Consequently, the analysis of hydrocarbon samples, before the industrial exploitation of the deposit or in the context of the design of recovery techniques (Enhanced Oil Recovery), is henceforth undeniable. This consists of simulating and/or reproducing the thermodynamic conditions to which the hydrocarbons will be subjected during their extraction so as to assess, as a function of their composition, the risks related to the potential appearance of solid phases.

The analysis methods commonly used for biphasic fluids are based on measuring optical properties and, in particular, the diffraction and/or absorption by the solid particles within the analyzed fluid.

For petroleum fluids, the measurements are generally done either using a microscope or by lighting the sample using a laser beam in the infrared wavelengths and measuring the optical power transmitted and/or absorbed through said sample.

The absorption factor (absorbed light) or, conversely, the transmission factor (transmitted light) varies as a function both of the density of the fluid (related to the pressure and temperature conditions) and the presence (optionally also the quantity) of solid particles (asphaltenes, for example).

Regarding the equipment, the known analysis cells generally comprise a cylinder in which an axially translatable piston is mounted that defines, with the end walls of the cylinder, a compression chamber in which the sample is subjected to a very high pressure while it is analyzed optically.

However, although the theoretical foundations of this detection method are well-established at this time, there is no equipment for implementing this method that is capable of precisely determining the appearance and/or levels of solid matter in petroleum fluids with extreme densities (heavy oils).

In fact, for the specific fluids, the density is such that, even with small sample volumes and high light powers, the precision of the measurements is quite insufficient.

SUMMARY OF THE INVENTION

The present invention aims to resolve these technical problems in a satisfactory manner by proposing a solution making it possible to offer reliability and precision of the measurements of the quantity of solid matter, irrespective of the volumes and the densities or viscosities of the samples.

This aim is achieved, according to the invention, using a cell characterized in that the walls of said chamber are provided with at least one bore designed for sealably receiving an optical measuring element movable inside said chamber between a retracted position retracted in the bore to allow the piston to pass, and a measuring position in which it protrudes in said chamber.

According to one advantageous feature, said measuring element comprises an optical fiber segment connected upstream to a laser source and cooperating downstream with the detector.

According to another advantageous feature, the inner end of the measuring element is connected to a collimator.

Preferably, said measuring element is housed in a sheath provided on the one hand with a peripheral sealing member and an inner sealing member and, on the other hand, captured in an outer support mandrel.

According to a first alternative of the invention, said peripheral sealing member is formed by a series of deformable rings.

According to another alternative, said inner sealing member is formed by brazing the rim of the sheath.

According to one specific feature, at least one of said mandrels is rotatable in a threading of the cylinder so as to ensure the translation of the associated coupling element.

Preferably, said mandrel is secured to a manual adjustment wheel.

According to one specific alternative, said bore is oriented in a diametrical axis of the cylinder.

According to another alternative, the cell comprises two opposite bores each designed to receive an optical measuring element, the first element forming a transmitter while the second element forms a receiver.

In that case, at least one of the two measuring elements is translatable across from the other element.

According to still another alternative, the longitudinal end wall of the chamber is made up of a viewing porthole.

Another object of the invention is a method for detecting the presence and/or measuring the quantity of solid particles or measuring the quantity of solid matter in a hydrocarbon sample by using an analysis cell of the type defined above.

This cell also enables the simultaneous implementation of a measuring step consisting of determining the saturation conditions of the fluid sample, more commonly called the "bubble point."

The cell according to the invention offers reliable and effective measuring means for quite varied hydrocarbon samples and in different capacities (from 10 to 2000 cm$^3$).

Although the pressure prevailing in the compression chamber is very high (approximately 150 MPa) and despite the presence in its wall of at least one bore, the sealing is not deteriorated and is, on the contrary, kept at its highest level owing to the peripheral and inner sealing members, respectively.

The presence of these bores in the side wall of the cylinder makes it possible to preserve the cylindrical profile of the compression chamber. This arrangement leaves the piston completely free in its travel and facilitates the agitation of the fluid sample in the chamber. It is thus possible to achieve very high pressure levels in the chamber for so-called "PVT" measurements through the viewing porthole and without creating dead space.

The presence of a porthole also makes it possible to perform PVT measurements and optical measurements simultaneously without creating any interaction.

Lastly, the possibility of moving the measuring elements to place them at the heart of the sample or to bring them closer together enables very precise analysis of very dense petroleum fluids whereof the opacity was able to constitute an error factor in the measurements.

BRIEF DESCRIPTION OF THE DRAWINGS

The invention will be better understood upon reading the following description, accompanied by the drawings, in which:

FIGS. 2A and 2B show partial longitudinal cross-sectional views of the embodiment of FIG. 1 with the optical detection elements in the retracted position and in the measuring position, respectively.

DETAILED DESCRIPTION

Figure 1:
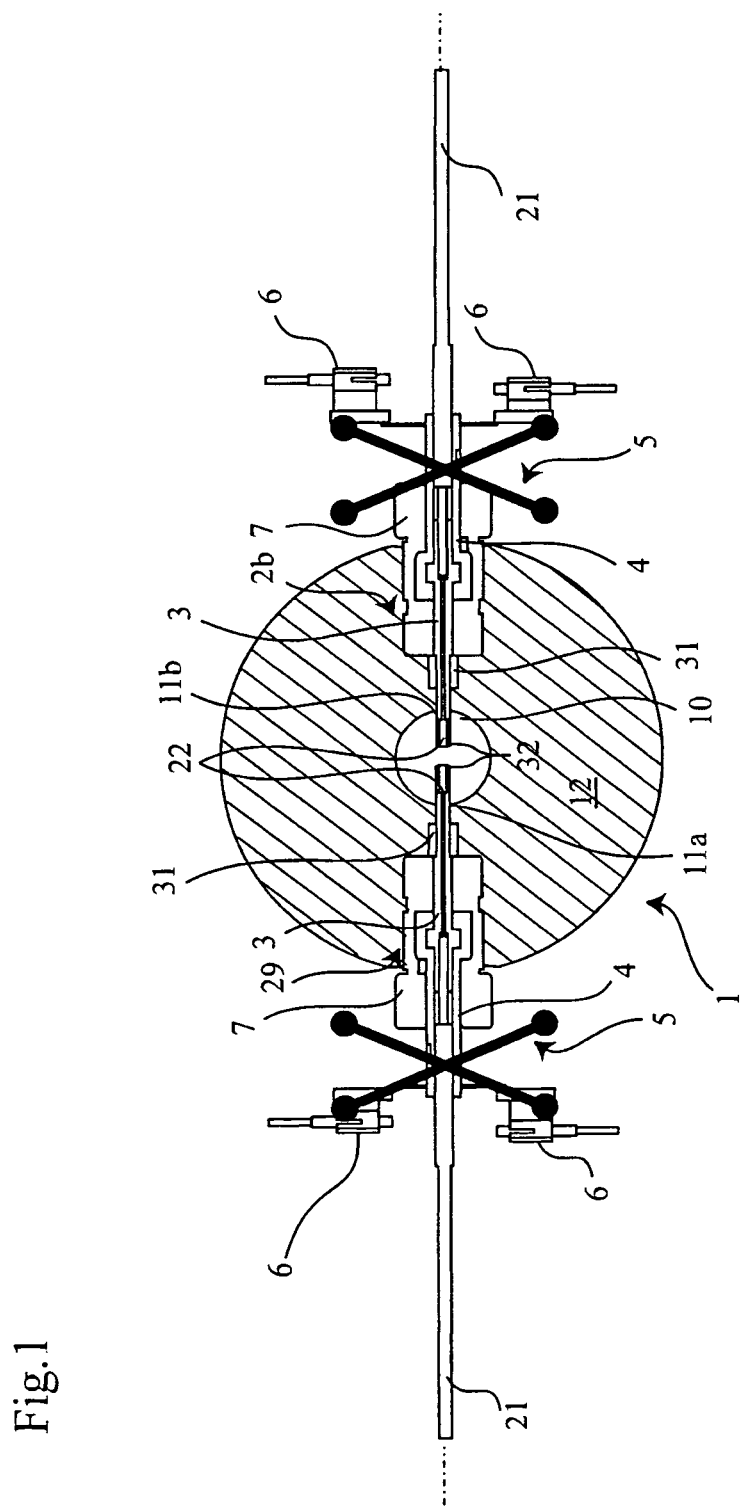
FIG. 1 shows a partial diagrammatic transverse cross-sectional view of one embodiment of the cell according to the invention.

The analysis cell shown in the figures is designed to determine the thermodynamic properties of hydrocarbons and, more particularly, to study their behavior under extreme pressure, volume and temperature (PVT) conditions as well as to detect and/or measure the quantity of solid particles present in those hydrocarbons under the same conditions. It comprises a cylindrical body 1 in which a piston (not shown) is housed axially translatably that defines, with the end walls of the cylinder, a compression chamber 10 designed to receive, in a confined manner, a sample of the hydrocarbon to be studied.

The chamber 10 is designed so as to be able to withstand pressures of approximately 150 MPa and temperatures of approximately 250° C. The structure of the cylinder 1, and in particular the thickness of its walls 12, is dimensioned accordingly.

The cell is traditionally equipped with all of the means (motors, cylinders, injection and extraction pumps, sensors, computers, etc.) in particular enabling the movement of the piston, the introduction of the sample and the cell, as well as the adjustment and monitoring of the thermodynamic parameters. These means, which are used in the operation of the cell, are traditional and are not the subject-matter of the invention.

The side wall 12 of the cylinder 1 is provided, at the chamber 10, above the idle position of the piston, with at least one bore 11 and, in the illustrated alternative, with two bores 11a, 11b across from each other.

These bores pass all the way through the wall 12 cylinder 1 and are designed for each sealably receiving an optical measuring element 2.

At least one of the measuring elements 2 can be moved inside the chamber 10 between a retracted position retracted in the bore 11 to allow the piston to pass (FIG. 2A) and a measuring position in which it protrudes in said chamber (FIG. 2B).

The telescoping nature of the measuring element makes it possible to adjust the position of the active end thereof in the chamber and to place it at an optimal location for measurements at the heart of the sample.

These detection and/or measurement elements 2 comprise, traditionally and as shown in FIG. 3, an optical fiber segment 21 connected upstream to a laser source (not shown) and cooperating downstream with a detector (not shown). The inner end of the measuring elements, and therefore here of the fiber, is optically connected to a sapphire collimator 22. An electronic microscope may advantageously complete the equipment, in particular, for specific measurement operations of the quantity of solid matter.

In the alternative of the cell illustrated in FIGS. 1, 2A and 2B, it is provided that the two measuring elements 2a, 2b are coupled to each other. At least one of the two elements 2a, 2b, and preferably both elements, are movable, translatably on their shared axis, which here is combined with the diameter of the chamber. In this alternative, the respective collimators 22 of each element 2a, 2b therefore face each other.

The first element 2a forms a transmitter, while the second element 2b forms a receiver. During the detection phase, the laser beam guided by the fiber 21 then passes in the collimator 22 of the element 2a, where it is oriented toward the chamber 10, then through the fluid hydrocarbon sample while lighting the suspended solid particles whereof the presence and/or concentration is determined by measuring diffraction and absorption phenomena of the optical signal upon reception in the element 2b.

This arrangement is interesting in the analysis of petroleum fluids with a high density, and therefore high opacity for which the optimization and precision of the optical measurements require bringing the transmitter closer to the receiver.

In the case where the cell only comprises a single measuring element 2, it is possible to provide that the opposite wall of the chamber 10 has a detection or reflection area cooperating with the transmitted beam. In this alternative, the single measuring element may then incorporate a transmitter and a detector of the reflected optical signal that are housed in the same bore.

Each measuring element 2 is housed in a sheath 3 provided on the one hand with a peripheral sealing member 31 and an inner sealing member 32, and on the other hand held captive by an outer support mandrel 4. The mandrel 4 is in turn engaged in a high-pressure connector 7 that is fastened in a cavity of the wall 12 of the body of the cell.

The peripheral sealing member 31 is made up of a series of attached deformable rings. The inner sealing member 32 is made up of a brazing of the rib of the sheath 3, at the connection with the fiber 21 and/or the collimator 22, which is also held captive inside the sheath.

The support mandrel 4 is rotatable in a threading formed in the connector 7 so as to translate the corresponding measuring element 2. This mandrel 4 is secured to a manual adjustment wheel 5 associated with a set of stops making it possible to ensure that the measuring element 2 reaches the retracted position, at the end of the retraction travel of the mandrel. The set of stops is actuated by a mechanical connection working by contact with the mandrel traditionally or by electrical/electronic connection by means of a detector 6 detecting the position of the mandrel 4 (see FIG. 1).

In one alternative not shown, it is possible to provide that the telescoping movement of the measuring element is ensured by sliding in a conduit.

The longitudinal end wall of the chamber 10 is covered by a viewing porthole (not shown) made from quartz or sapphire, transparent to visible light and connected sealably to the side wall of the cylinder 1. This porthole makes it possible, in parallel and simultaneously with the method according to the invention relative to the detection of solid matter, to measure saturation conditions additionally using, for example, an endoscope optionally associated with a video camera.

The invention claimed is:

1. An analysis cell for the analysis, at very high pressure and high temperature, of fluid samples comprising a cylinder in which an axially translatable piston is housed that defines, with walls of the cylinder, a closed compression chamber in which the sample is confined, wherein a side wall of said chamber is provided with at least one first bore designed for sealably receiving a first measuring element movable inside said chamber between a retracted position retracted into the bore to allow the piston to pass by the measuring element, and a measuring position in which the measuring element protrudes into said closed compression chamber.

2. The analysis cell according to claim 1, wherein said measuring element comprises an optical fiber segment connected upstream to a laser source and cooperating downstream with a detector.

3. The analysis cell according to claim 1, wherein an inner end of the measuring element is connected to a collimator.

4. The analysis cell according to claim 1, wherein said measuring element is housed in a sheath provided on one side with a peripheral sealing member and an inner sealing member and, on another side, captured in an outer support mandrel.

5. The analysis cell according to claim 4, wherein said peripheral sealing member is formed by a plurality of deformable rings.

6. The analysis cell according to claim 4, wherein said inner sealing member is formed by brazing a rim of the sheath.

7. The analysis cell according to claim 4, wherein said mandrel is rotatable in a threading formed in the side wall of the cylinder to enable the translation of the measuring element.

8. The analysis cell according to claim 7, wherein said mandrel is secured to a manual adjustment wheel.

9. The analysis cell according to claim 1, wherein said bore is oriented in a diametrical axis of the cylinder.

10. The analysis cell according to claim 1, wherein the analysis cell comprises a second bore diametrically opposite the first bore designed to sealably receive a second measuring element, the first measuring element forming a transmitter and the second measuring element forming a receiver.

11. The analysis cell according to claim 10, wherein at least one of the first and second measuring elements is translatable across from the remaining element.

12. The analysis cell according to claim 1, wherein a longitudinal end wall of the chamber includes a viewing porthole.

13. A method for detecting the presence or measuring the quantity of solid particles or measuring the quantity of solid matter in a hydrocarbon sample, wherein an analysis cell according to claim 1 is used.

14. The method according to claim 13, wherein saturation conditions and bubble point of the sample are determined simultaneously.

* * * * *